US011534231B2

(12) United States Patent
Ding et al.

(10) Patent No.: US 11,534,231 B2
(45) Date of Patent: Dec. 27, 2022

(54) ENERGY-BASED SURGICAL INSTRUMENTS AND SYSTEMS CONFIGURED TO MINIMIZE THERMAL SPREAD

(71) Applicant: COVIDIEN LP, Mansfield, MA (US)

(72) Inventors: Weijiang Ding, Shanghai (CN); Ming Cao, Jiangsu (CN); Yuanxun Li, Shanghai (CN); Pu Liu, Shanghai (CN)

(73) Assignee: CovidienLP, Mansfield, MA (US)

( * ) Notice: Subject to any disclaimer, the term of this patent is extended or adjusted under 35 U.S.C. 154(b) by 1202 days.

(21) Appl. No.: 16/070,003

(22) PCT Filed: Aug. 22, 2017

(86) PCT No.: PCT/CN2017/098435
§ 371 (c)(1),
(2) Date: Jul. 13, 2018

(87) PCT Pub. No.: WO2019/036896
PCT Pub. Date: Feb. 28, 2019

(65) Prior Publication Data
US 2021/0212751 A1 Jul. 15, 2021

(51) Int. Cl.
*A61B 18/14* (2006.01)
*A61B 17/32* (2006.01)
*A61B 17/00* (2006.01)

(52) U.S. Cl.
CPC .. *A61B 18/1445* (2013.01); *A61B 17/320092* (2013.01); *A61B 2017/00734* (2013.01);
(Continued)

(58) Field of Classification Search
CPC ........ A61B 18/1445; A61B 17/320092; A61B 2017/00734; A61B 2017/32007;
(Continued)

(56) References Cited

U.S. PATENT DOCUMENTS 3,916,909 A * 11/1975 Kletschka ............... A61B 17/30
604/35
4,074,718 A * 2/1978 Morrison, Jr. ..... A61B 18/1402
219/145.21
(Continued)

FOREIGN PATENT DOCUMENTS

CN 101511286 A 8/2009
CN 201939898 U 8/2011
(Continued)

OTHER PUBLICATIONS

Notification of Transmittal of the International Search Report and the Written Opinion of the International Searching Authority, or the Declaration issued in corresponding PCT Application No. PCT/CN2017/098435 dated May 22, 2018, 12 pages.
(Continued)

*Primary Examiner* — Michael F Peffley
*Assistant Examiner* — Amanda L Zink
(74) *Attorney, Agent, or Firm* — Carter, DeLuca & Farrell LLP (57) ABSTRACT

A surgical instrument includes an end effector assembly including first and second grasping components each defining a tissue-contacting portion. One or both of the grasping components is movable relative to the other to a closed position wherein the tissue-contacting portions cooperate to define a grasping area therebetween. One or both of the grasping components is configured to apply energy from the tissue-contacting portion thereof to tissue disposed within the grasping area to treat tissue. The tissue-contacting portion of the first grasping component defines a first opening disposed within the grasping area and in communication with a first lumen defined at least partially through the first grasping component. The first lumen is adapted to connect
(Continued)

to a source of vacuum to enable aspiration through the first opening.

18 Claims, 6 Drawing Sheets

(52) U.S. Cl.
CPC ............ *A61B 2017/32007* (2017.08); *A61B 2017/320093* (2017.08); *A61B 2218/007* (2013.01)

(58) Field of Classification Search
CPC .. A61B 2017/320093; A61B 2218/007; A61B 2017/2825; A61B 2017/306; A61B 2017/32008; A61B 2018/0063; A61B 2018/00994; A61B 2217/005; A61B 18/1442; A61B 17/320068; A61B 18/12; A61B 2017/320072; A61B 2017/320082; A61B 2018/00005; A61B 2018/1452
See application file for complete search history.

(56) References Cited

U.S. PATENT DOCUMENTS

| | | | |
|---|---|---|---|
| 4,096,864 A * | 6/1978 | Kletschka | A61B 17/30 604/35 |
| 4,681,561 A | 7/1987 | Hood et al. | |
| 4,724,834 A | 2/1988 | Alperovich et al. | |
| 5,190,541 A * | 3/1993 | Abele | A61B 18/1442 604/35 |
| 5,217,460 A * | 6/1993 | Knoepfler | A61B 17/29 606/1 |
| 5,250,075 A * | 10/1993 | Badie | A61B 17/30 606/207 |
| 5,383,876 A | 1/1995 | Nardella | |
| 5,391,144 A | 2/1995 | Sakurai et al. | |
| 5,603,712 A * | 2/1997 | Koranda | A61B 18/1442 604/35 |
| 5,797,958 A * | 8/1998 | Yoon | A61F 6/20 606/139 |
| 6,206,876 B1 | 3/2001 | Levine et al. | |
| 6,379,371 B1 | 4/2002 | Novak et al. | |
| 6,764,487 B2 | 7/2004 | Mulier et al. | |
| 6,939,350 B2 | 9/2005 | Phan | |
| 7,074,219 B2 | 7/2006 | Levine et al. | |
| 8,348,880 B2 * | 1/2013 | Messerly | A61B 17/320092 604/22 |
| 8,469,957 B2 * | 6/2013 | Roy | A61B 18/1445 606/51 |
| 9,138,285 B2 * | 9/2015 | Sutter | A61M 1/84 |
| 9,173,707 B2 * | 11/2015 | Singh | A61B 18/18 |
| 9,764,166 B2 | 9/2017 | Stoddard et al. | |
| 9,788,882 B2 * | 10/2017 | Evans | A61B 18/1442 |
| 10,987,159 B2 * | 4/2021 | Ding | A61B 18/1445 |
| 2002/0091404 A1 | 7/2002 | Beaupre | |
| 2003/0181904 A1 | 9/2003 | Levine et al. | |
| 2003/0204199 A1 | 10/2003 | Novak et al. | |
| 2005/0209578 A1 | 9/2005 | Christian Evans et al. | |
| 2006/0265035 A1 * | 11/2006 | Yachi | A61B 17/320092 607/101 |
| 2007/0233054 A1 | 10/2007 | Babaev | |
| 2008/0015563 A1 | 1/2008 | Hoey et al. | |
| 2009/0036914 A1 | 2/2009 | Houser | |
| 2010/0087814 A1 * | 4/2010 | Desinger | A61B 18/1442 606/45 |
| 2010/0087816 A1 * | 4/2010 | Roy | A61B 18/1445 606/48 |
| 2012/0078278 A1 | 3/2012 | Bales, Jr. et al. | |
| 2012/0253371 A1 | 10/2012 | Ross et al. | |
| 2013/0046337 A1 | 2/2013 | Evans et al. | |
| 2013/0072950 A1 | 3/2013 | Ross et al. | |
| 2013/0178842 A1 | 7/2013 | Reid, Jr. | |
| 2014/0276369 A1 | 9/2014 | Banko | |
| 2015/0080876 A1 * | 3/2015 | Worrell | A61B 18/1445 606/34 |
| 2015/0141980 A1 | 5/2015 | Jadhav et al. | |
| 2017/0105752 A1 * | 4/2017 | Boudreaux | A61B 17/320092 |
| 2017/0105789 A1 * | 4/2017 | Boudreaux | A61B 18/1445 |

FOREIGN PATENT DOCUMENTS

| | | |
|---|---|---|
| EP | 00514810 A1 | 11/1992 |
| EP | 2572660 A2 | 3/2013 |
| JP | S62177415 A | 8/1987 |
| JP | H01151452 | 6/1989 |
| JP | 2005160735 A | 6/2005 |
| JP | 04089043 B2 | 5/2008 |
| JP | 2014000311 A | 1/2014 |
| JP | 2014233540 A | 12/2014 |
| WO | 2009032438 A2 | 3/2009 |
| WO | 2014196226 A1 | 12/2014 |

OTHER PUBLICATIONS

Extended European Search Report issued in EP Application No. 18189867.7 dated Dec. 19, 2018, 8 pages.

\* cited by examiner

ENERGY-BASED SURGICAL INSTRUMENTS AND SYSTEMS CONFIGURED TO MINIMIZE THERMAL SPREAD

FIELD OF THE INVENTION

The present disclosure relates to surgical instruments and systems and, more particularly, to energy-based surgical instruments and systems configured to minimize thermal spread.

BACKGROUND OF THE INVENTION

Energy-based surgical instruments utilize energy to affect hemostasis by heating tissue to treat tissue. Energy-based surgical instruments, more specifically, may be configured to utilize both mechanical clamping action and energy, e.g., radiofrequency (RF) energy, ultrasonic energy, light energy, microwave energy, thermal energy, etc., to affect hemostasis by heating tissue to treat, e.g., coagulate, cauterize, and/or seal, tissue.

SUMMARY OF THE INVENTION

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

Provided in accordance with aspects of the present disclosure is a surgical instrument including an end effector including first and second grasping components each defining a tissue-contacting portion. One or both of the first or second grasping components is movable relative to the other between an open position and a closed position. In the closed position, the first and second tissue-contacting portions cooperate to define a grasping area therebetween. One or both of the first or second grasping components is configured to apply energy from the tissue-contacting portion thereof to tissue disposed within the grasping area to treat tissue. The tissue-contacting portion of the first grasping component defines a first opening therethrough. The first opening is disposed within the grasping area and in communication with a first lumen defined at least partially through the first grasping component. The first lumen is adapted to connect to a source of vacuum to enable aspiration through the first opening.

In an aspect of the present disclosure, the tissue-contacting portion of the second grasping component defines a second opening therethrough. The second opening is disposed within the grasping area and in communication with a second lumen defined at least partially through the second grasping component. The second lumen is adapted to connect to a source of vacuum to enable aspiration through the second opening.

In another aspect of the present disclosure, the tissue-contacting portion of the first grasping component is configured to conduct radiofrequency (RF) energy through tissue disposed within the grasping area and to the tissue-contacting portion of the second grasping component.

In another aspect of the present disclosure, the tissue-contacting portion of the first grasping component is configured to supply ultrasonic energy to tissue disposed within the grasping area.

In such aspects, the second grasping component may include a structural body having a jaw liner engaged therewith. The jaw liner defines the tissue-contacting portion of the second grasping component.

In still another aspect of the present disclosure, the tissue-contacting portion of the first grasping component defines a plurality of first openings therethrough. The plurality of first openings are spaced longitudinally along a length of the tissue-contacting portion of the first grasping component.

In yet another aspect of the present disclosure, the surgical instrument further includes a housing and at least one shaft extending distally from the housing and supporting the end effector assembly at a distal end portion thereof. In such aspects, the first lumen communicates with a shaft lumen extending through the at least one shaft and the shaft lumen is adapted to connect to a source of vacuum to enable aspiration through the first opening.

In still yet another aspect of the present disclosure, the surgical instrument further includes first and second shafts pivotably coupled to one another and supporting the end effector assembly at distal end portions thereof. In such aspects, the first lumen communicates with a first shaft lumen extending through the first shaft. The first shaft lumen is adapted to connect to a source of vacuum to enable aspiration through the first opening.

A radiofrequency (RF) surgical instrument provided in accordance with aspects of the present disclosure includes an end effector assembly including first and second jaw members each defining a tissue-contacting portion. One or both of the first or second jaw members is movable relative to the other between an open position and a closed position. In the closed position, the first and second tissue-contacting portions cooperate to define a grasping area therebetween. The first and second jaw members are adapted to connect to a source of RF energy to conduct RF energy between the tissue-contacting portions and through tissue grasped within the grasping area to treat tissue. The tissue-contacting portion of the first jaw member defines a first opening therethrough disposed within the grasping area and in communication with a first lumen defined at least partially through the first jaw member. The first lumen is adapted to connect to a source of vacuum to enable aspiration through the first opening.

In an aspect of the present disclosure, the tissue-contacting portion of the second jaw member defines a second opening therethrough. The second opening is disposed within the grasping area and in communication with a second lumen defined at least partially through the second jaw member. The second lumen is adapted to connect to a source of vacuum to enable aspiration through the second opening.

In another aspect of the present disclosure, the tissue-contacting portion of the first jaw member defines a first tissue contacting surface, a second tissue-contacting surface, and a wall disposed between the first and second tissue-contacting surfaces. The first opening is defined through the wall in such aspects. The first and second tissue-contacting surfaces, in such aspects, may be offset relative to one another via a step.

In yet another aspect of the present disclosure, the RF surgical instrument further includes first and second shafts pivotably coupled to one another and supporting the first and second jaw members, respectively, at respective distal end portions thereof. In such aspects, the first lumen communicates with a first shaft lumen extending through the first shaft. The first shaft lumen is adapted to connect to a source of vacuum to enable aspiration through the first opening.

In still another aspect of the present disclosure, one of the first or second shafts supports a housing thereon at a proximal end portion thereof. The housing includes an activation button that is selectively activatable to supply RF energy to the first and second jaw members.

An ultrasonic surgical instrument provided in accordance with aspects of the present disclosure includes an ultrasonic waveguide defining an ultrasonic blade at a distal end portion thereof.

The ultrasonic waveguide is configured to transmit ultrasonic energy therealong to the ultrasonic blade. The ultrasonic surgical instrument further includes a jaw member pivotable relative to the ultrasonic blade between an open position and a closed position. The jaw member includes a structural body and a jaw liner retained by the structural body. The jaw liner defines a tissue-contacting surface, wherein, in the closed position, the tissue-contacting surface of the jaw liner and an opposed surface of the ultrasonic blade cooperate to define a grasping area therebetween. The ultrasonic blade and/or the jaw liner defines an opening therethrough. The opening is disposed within the grasping area and in communication with a lumen defined at least partially through the ultrasonic blade and/or the jaw liner. The lumen is adapted to connect to a source of vacuum to enable aspiration through the opening.

In an aspect of the present disclosure, the ultrasonic waveguide defines the lumen extending therethrough and into the ultrasonic blade. In such aspects, the ultrasonic blade defines the opening therethrough in communication with the lumen.

In another aspect of the present disclosure, the jaw liner defines the lumen such that the lumen has an open proximal end portion and a closed distal end portion. In such aspects, the jaw liner defines the opening therethrough in communication with the lumen.

In yet another aspect of the present disclosure, the ultrasonic surgical instrument further includes a housing and an elongated assembly extending distally from the housing and supporting the end effector assembly at a distal end portion thereof. In such aspects, the lumen communicates with a shaft lumen extending through the elongated assembly. The shaft lumen is adapted to connect to a source of vacuum to enable aspiration through the opening.

In still another aspect of the present disclosure, the ultrasonic surgical instrument further includes a transducer and generator assembly disposed on or in the housing and a battery assembly disposed on or in the housing. The battery assembly is configured to power the transducer and generator assembly to, in turn, produce ultrasonic energy for transmission along the ultrasonic waveguide.

In still yet another aspect of the present disclosure, a vacuum system is disposed on or within the housing. The vacuum system is configured to enable aspiration through the first opening.

BRIEF DESCRIPTION OF THE DRAWINGS

Various aspects and features of the present disclosure are described herein with reference to the drawings wherein.

DETAILED DESCRIPTION OF THE EMBODIMENTS

The present disclosure relates to energy-based surgical instruments configured to reduce or eliminate thermal spread. An exemplary radiofrequency (RF) surgical forceps 100 (FIG. 1) and an exemplary ultrasonic surgical instrument 1000 (FIG. 4) are detailed herein exemplifying the aspects and features of the present disclosure; however, the present disclosure is equally applicable for use with any suitable energy-based surgical instrument. Further, although RF surgical forceps 100 (FIG. 1) is shown as a hemostat-style instrument and ultrasonic surgical instrument 1000 (FIG. 4) is shown as a shaft-based instrument, this configuration may be reversed, e.g., wherein the RF instrument is of a shaft-based style and the ultrasonic surgical instrument is of a hemostat-style. Obviously, different electrical and mechanical considerations apply to each particular type and/or style of instrument; however, the aspects and features of the present disclosure remain generally consistent regardless of the particular energy-based surgical instrument used.

Figure 1:
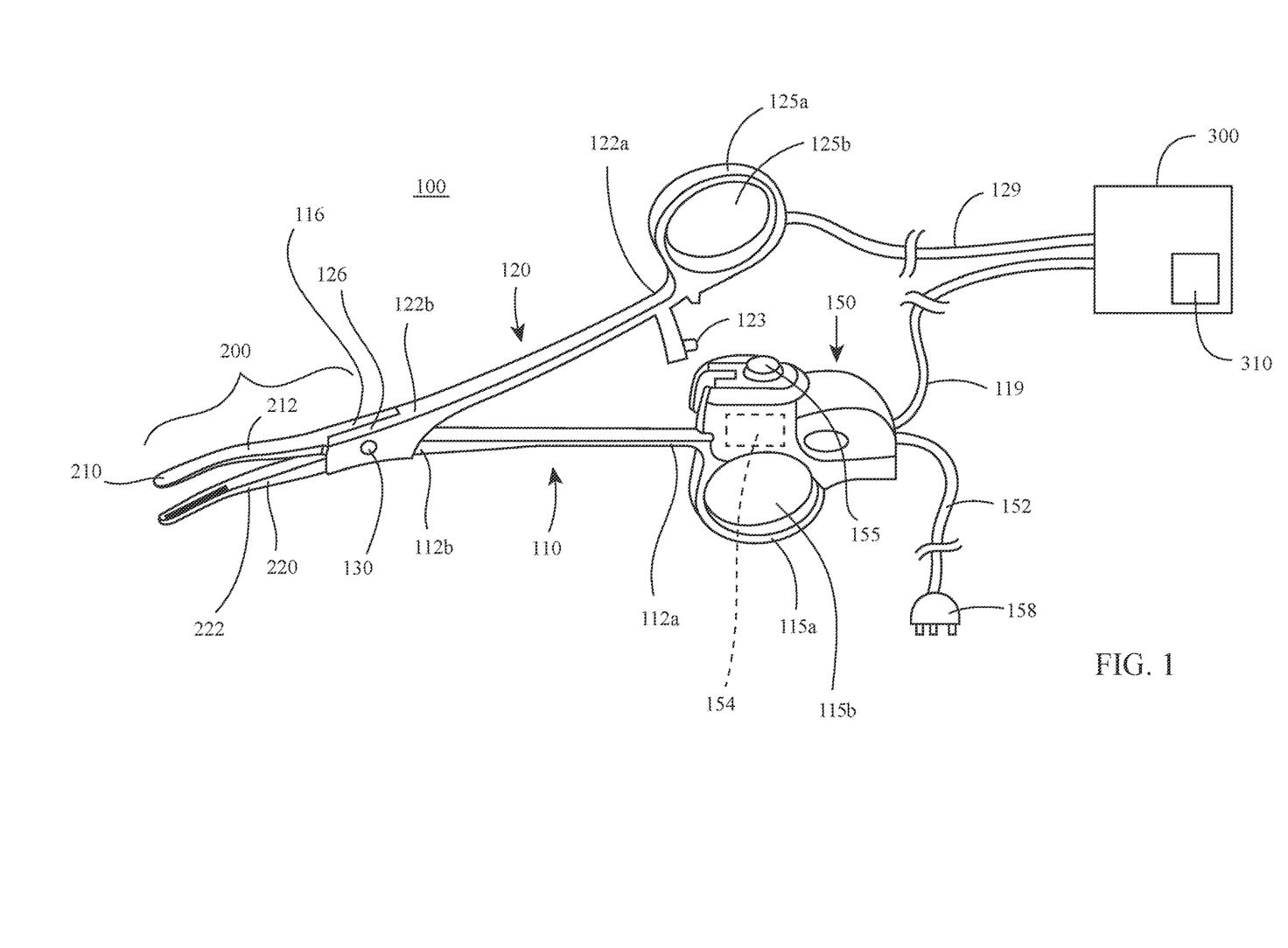
FIG. 1 is a side, perspective view of a radiofrequency (RF) surgical system including a surgical forceps and an electrosurgical generator in accordance with the present disclosure.

Referring to FIG. 1, RF surgical forceps 100 provided in accordance with the present disclosure includes first and second shaft members 110, 120 each having a proximal end portion 112a, 122a and a distal end portion 112b, 122b, respectively. An end effector assembly 200 of forceps 100 includes first and second jaw members 210, 220 extending from distal end portions 112b, 122b of shaft members 110, 120, respectively. Forceps 100 further includes a pivot 130 pivotably coupling first and second shaft members 110, 120 with one another, and a housing 150 engaged with the proximal end portion of one of the shaft members, e.g., proximal end portion 112a of shaft member 110. A cable 152 extends from housing 150 to couple forceps 100 to an electrosurgical generator (not shown) to enable the supply of RF energy to forceps 100, while tubes 119, 129 extend from proximal end portions 112a, 122a, respectively, of shaft members 110, 120, respectively, to couple forceps 100 to a vacuum source 300, as detailed below. In embodiments, the electrosurgical generator and vacuum source 300 may be provided as a single unit. In embodiments, the electrosurgical generator and/or vacuum source 300 may be remote from forceps 100 or may be mounted thereon or therein.

Shaft members 110, 120 are formed at least partially from an electrically-conductive material such that electrosurgical energy may be transmitted therealong to and from jaw members 210, 220, respectively. Alternatively, shaft members 110, 120 may house conductors (not shown) configured to transmit electrosurgical energy to and from jaw members 210, 220. Proximal end portions 112a, 122a of shaft members 110, 120, respectively, include handles 115a, 125a defining finger holes 115b, 125b configured to facilitate grasping and manipulating shaft members 110, 120.

Figure 3A:
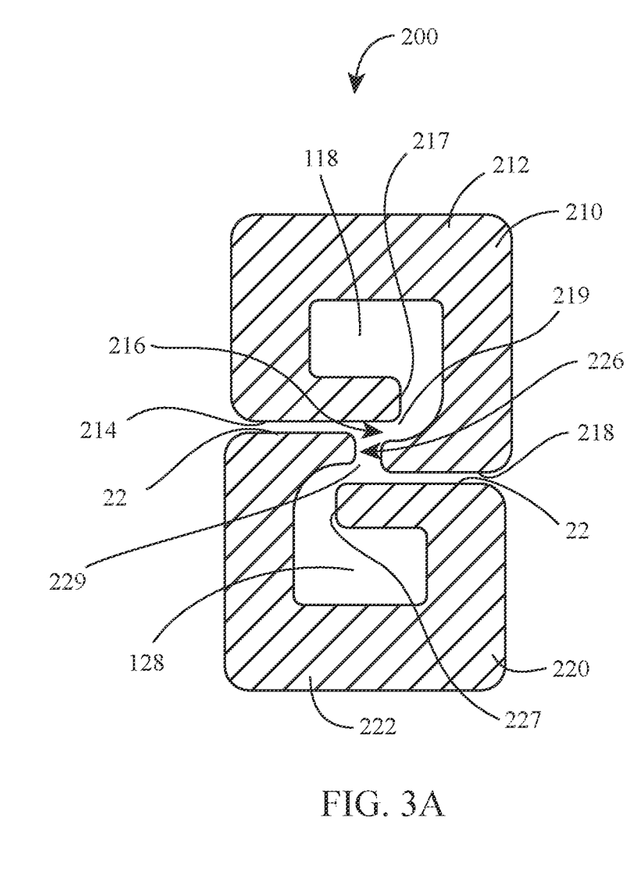
FIG. 3A is a transverse, cross-sectional view of jaw members of the surgical forceps of FIG. 1, disposed in a closed position.

Distal end portions 112b, 122b of shaft members 110, 120 form uprights 116, 126 defining apertures configured to receive pivot 130 therethrough for pivotably coupling distal end portions 112b, 122b of shaft members 110, 120 with one another. As a result of this configuration, handles 115a, 125a are movable relative to one another in directions substantially perpendicular to a pivot axis of pivot 130 to move shaft members 110, 120 between a spaced-apart position and an approximated position to thereby pivot jaw members 210, 220 about pivot 130 and relative to one another between an open position (FIG. 1) and a closed position (FIG. 3A). Handles 115a, 125a are further movable relative to one another in directions substantially parallel to the pivot axis of pivot pin 130 to move shaft members 110, 120 from the approximated position to a yawed position to thereby move jaw members 210, 220 from the closed position (FIG. 3A) to a cutting position (FIG. 3B).

Referring still to FIG. 1, housing 150 is mounted, e.g., releasably mounted, on proximal end portion 112a of shaft member 110 and includes cable 152 extending proximally from therefrom and a switch assembly 154 having an activation button 155 extending from housing 150 towards shaft member 120. Cable 152 includes a plug 158 disposed at the free proximal end portion thereof to enable connection of forceps 100 to a source of energy (not shown), e.g., an electrosurgical generator. A plurality of electrical lead wires (not shown) extend through cable 152 and into housing 150, communicating with switch assembly 154 and first and second electrical contacts (not shown) disposed within housing 152. The first electrical contact is disposed in electrical communication with shaft member 110 to establish electrical communication between one or more of the plurality of electrical lead wires and first jaw member 210, while the second electrical contact is positioned such that, in the approximated position of shaft members 110, 120, respectively, an electrical connection pin 123 of shaft member 120 contacts the second electrical contact to establish electrical communication between one or more of the plurality of electrical lead wires and second jaw member 220. However, other suitable electrical connection arrangements are also contemplated.

Switch assembly 154 is positioned such that, upon movement of shaft members 110, 120 to the approximated position, handle 125a of shaft member 120 is sufficiently urged into contact with activation button 155 to actuate activation button 155. One of more of the plurality of electrical lead wires, as noted above, is coupled to switch assembly 154, thus enabling initiation of the supply of RF energy to jaw members 210, 220 of end effector assembly 200 upon actuation of activation button 155 of switch assembly 154, e.g., for treating tissue grasped between jaw members 210, 220.

Figure 2:
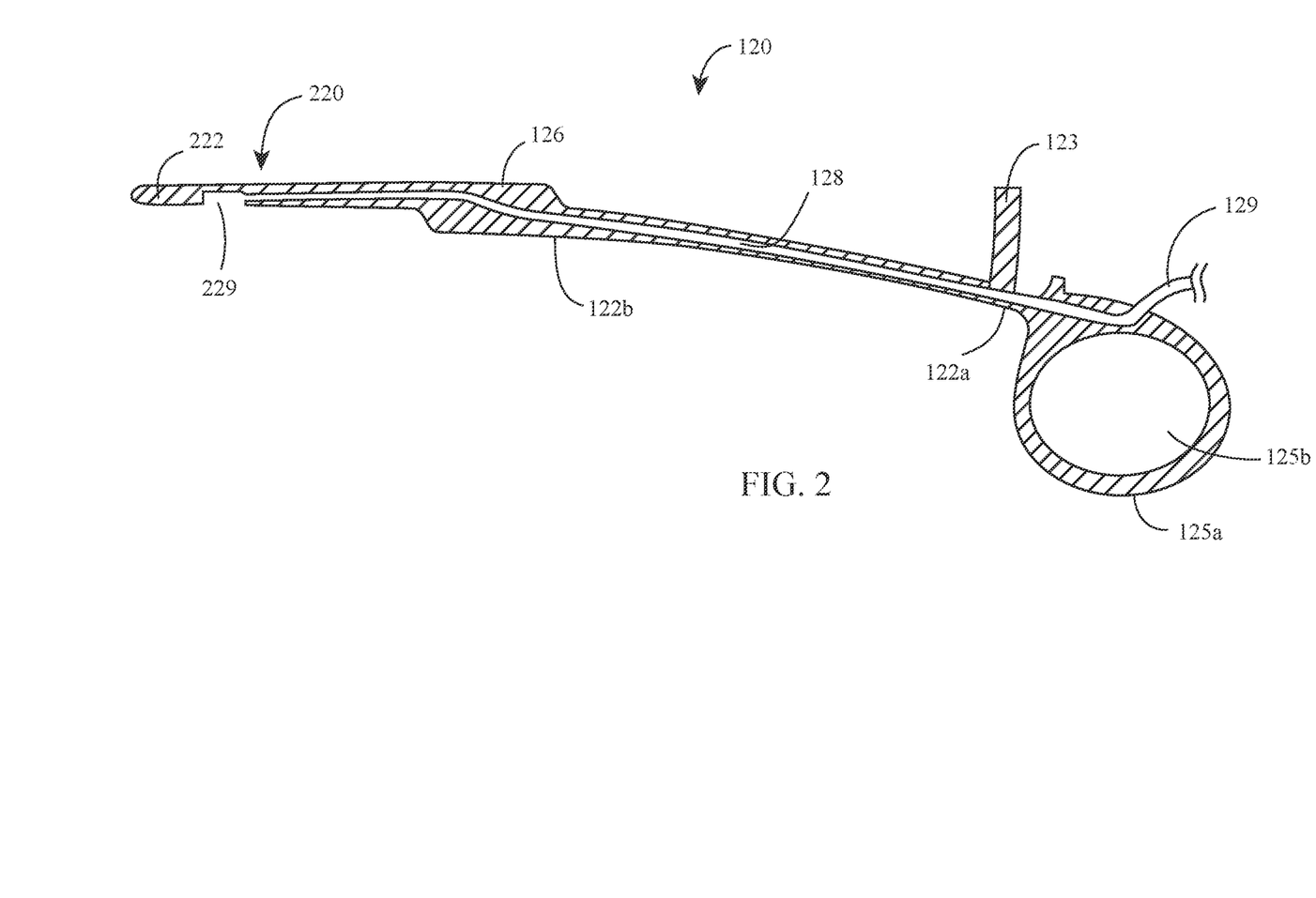
FIG. 2 is a longitudinal, cross-sectional view of one of the shaft members of the surgical forceps of FIG. 1.
Figure 3B:
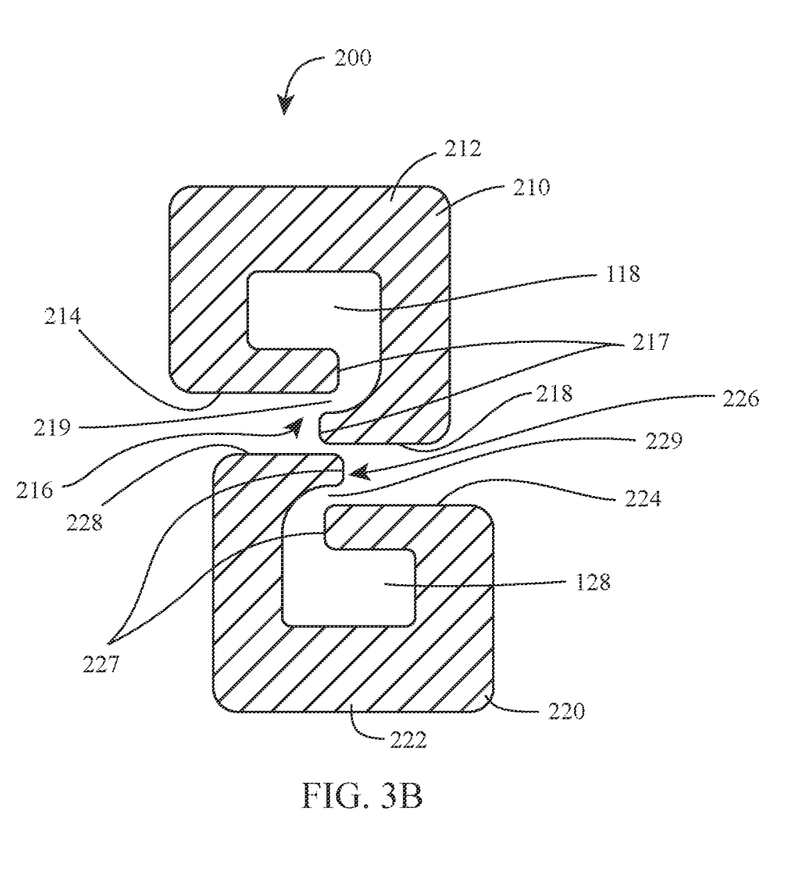
FIG. 3B is a transverse, cross-sectional view of the jaw members of the surgical forceps of FIG. 1, disposed in a cutting position.

Referring also to FIG. 2-3B, each shaft member 110, 120 defines a lumen 118, 128 extending longitudinally therethrough from proximal end portion 112a, 122a, through distal end portion 112b, 122b, respectively, thereof, and into the respective jaw member 210, 220 thereof. Although only shaft member 120 and lumen 128 thereof are illustrated in FIG. 2, it is understood that shaft member 110 defines a similar configuration. Lumens 118, 128 communicate with respective tubes 119, 129 at the proximal end portions 112a, 122a of shaft members 110, 120, respectively, such that lumens 118, 128 are disposed in operable communicate with vacuum source 300. As such, and as described in greater detail below, when vacuum source 300 is activated, a vacuum is applied through tubes 119, 129 and, thus, through lumens 118, 128.

End effector assembly 200, as mentioned above, includes first and second jaw members 210, 220 pivotable relative to one another between the open position (FIG. 1) and the closed position (FIG. 3A). Jaw members 210, 220 are further movable, as also noted above, to a cutting position (FIG. 3B).

Each jaw member 210, 220 includes a body 212, 222 defining a first tissue-contacting surface portion 214, 224, a step 216, 226 extending from the respective body 212, 222 towards the other jaw members 210, 220, and a second tissue-contact surface portion 218, 228, respectively offset relative to the respective first tissue-contacting surface portion 214, 224 via the respective step 216, 226. Steps 216, 226 of jaw members 210, 220 include walls 217, 227, respectively, interconnecting respective first and second tissue-contacting surface portions 114, 124 and 214, 224, of respective jaw members 210, 220 with one another. Walls 217, 227 extend in generally perpendicular orientation relative to each of the first and second tissue-contacting surface portions 114, 124 and 214, 224, respectively, of the corresponding jaw member 210, 220.

Steps 216, 226 are laterally offset relative to one another such that, in an aligned orientation of jaw members 210, 220, second tissue-contact surface portion 218 of jaw member 210 opposes a portion of first tissue-contacting surface portion 224 of jaw member 220 and such that second tissue-contact surface portion 228 of jaw member 220 opposes a portion of first tissue-contacting surface portion 214 of jaw member 210. Further, first tissue-contacting surface portions 214, 224 define greater widths as compared to second tissue-contacting surface portions 218, 228 such that the portions of first tissue-contacting surface portions 214, 224 extending between steps 216, 226 also oppose one another.

Walls 217, 227 of steps 216, 226 define openings 219, 229 therethrough in communication with lumens 118, 128. With openings 219, 229 defined through walls 217, 227, tissue-contacting surface portions 214, 218 and 224, 228, respectively, are uninterrupted. Each opening 219, 229 may be defined as a slot extending along the length of the respective step 216, 226, or may define a plurality of apertures spaced-apart along the length of the respective step 216, 226. Other configurations are also contemplated. With opening 219, 229 disposed in communication with respect lumens 118, 128, upon activation of vacuum source 300 (FIG. 1), negative pressure is created within lumens 118, 128 so as to provide aspiration through openings 219, 229 and lumens 118, 128. Vacuum source 300 may include a collection reservoir 310, or a separate collection reservoir (not shown) may be provided, to collect any fluids and tissue debris aspirated from the surgical site via openings 219, 229.

Continuing with reference to FIGS. 1-3B, in use, with shaft members 110, 120 disposed in the spaced-apart position (FIG. 1), jaw members 210, 220 are disposed in the open position of wherein jaw members 210, 220 are spaced-apart from one another and disposed in an aligned orientation relative to one another. In this position, forceps 100 may be manipulated such that tissue to be grasped, treated, and/or divided is disposed between jaw members 210, 220.

Once tissue to be grasped, treated, and/or divided is disposed between jaw members 210, 220, shaft members 110, 120 may be moved relative to one another in directions substantially perpendicular to the pivot axis of pivot 130 from the spaced-apart position to the approximated position to pivot jaw members 210, 220 about pivot 130 and relative to one another from the open position (FIG. 1) to the closed position (FIG. 3A). In the closed position of jaw members 210, 220, jaw members 210, 220 are approximated relative to one another but maintained in the aligned orientation. More specifically, second tissue-contact surface portion 218 of jaw member 210 is approximated relative to the opposing portion of first tissue-contacting surface portion 224 of jaw member 220 and second tissue-contact surface portion 228 of jaw member 220 is approximated relative to the opposing portion of first tissue-contacting surface portion 214 of jaw member 210.

Movement of jaw members 210, 220 between the open and closed positions (FIGS. 1 and 3A, respectively) may be effectuated in order to grasp and/or manipulate tissue. With tissue grasped between jaw members 210, 220 in the closed position thereof, RF energy may be conducted between jaw members 210, 220 to treat tissue grasped therebetween, e.g., upon actuation of activation button 155 (FIG. 1). More specifically, RF energy is conducted between second tissue-contact surface portion 218 of jaw member 210 and the opposing portion of first tissue-contacting surface portion 224 of jaw member 220 to treat, e.g., seal, tissue therebetween, and between second tissue-contact surface portion 228 of jaw member 220 and the opposing portion of first tissue-contacting surface portion 214 of jaw member 210 to treat, e.g., seal, tissue therebetween. RF energy may also be conducted transversely across the portions of first tissue-contacting surface portions 214, 224 extending between steps 216, 226 to treat, e.g., seal, tissue disposed therebetween.

As energy is conducted between jaw members 210, 220 to treat tissue, tissue grasped between jaw members 210, 220 is heated and, as a by-product thereof, high pressure and temperature steam may be produced. The high pressure and temperature steam may escape the area between jaw members 210, 220 and potentially thermally damage surrounding tissue. This is known as thermal spread.

In order to minimize or eliminate thermal spread, during the conduction of energy between jaw members 210, 220 (and, in embodiments, for a period after de-activation), vacuum source 300 may be activated to apply vacuum through tubes 119, 129, lumens 118, 128, and thus, at openings 219, 229. As a result, the high pressure and temperature steam, as well as other heated fluids and/or tissue debris, are aspirated through openings 219, 229, lumens 118, 128, and into collection reservoir 310, rather than spreading outwardly. Vacuum source 300 may be activated automatically upon activation of switch assembly 154, or manually.

Once tissue has been treated, shaft members 110, 120 may be moved relative to one another in directions substantially parallel to the pivot axis of pivot 130 from the approximated position to the yawed position to move jaw members 210, 220 relative to one another from the closed position (FIG. 3A) to the cutting position (FIG. 3B). In this manner, a shearing action between steps 216, 226 is effected to cut tissue disposed therebetween. As an alternative to the above-detailed cutting arrangement, one or both of jaw members 210, 220 may define a knife channel (not shown) configured to enable reciprocation of a knife (not shown) therethrough.

In such embodiments, openings 219, 229 may be defined through the walls defining the knife channel.

Figure 4:
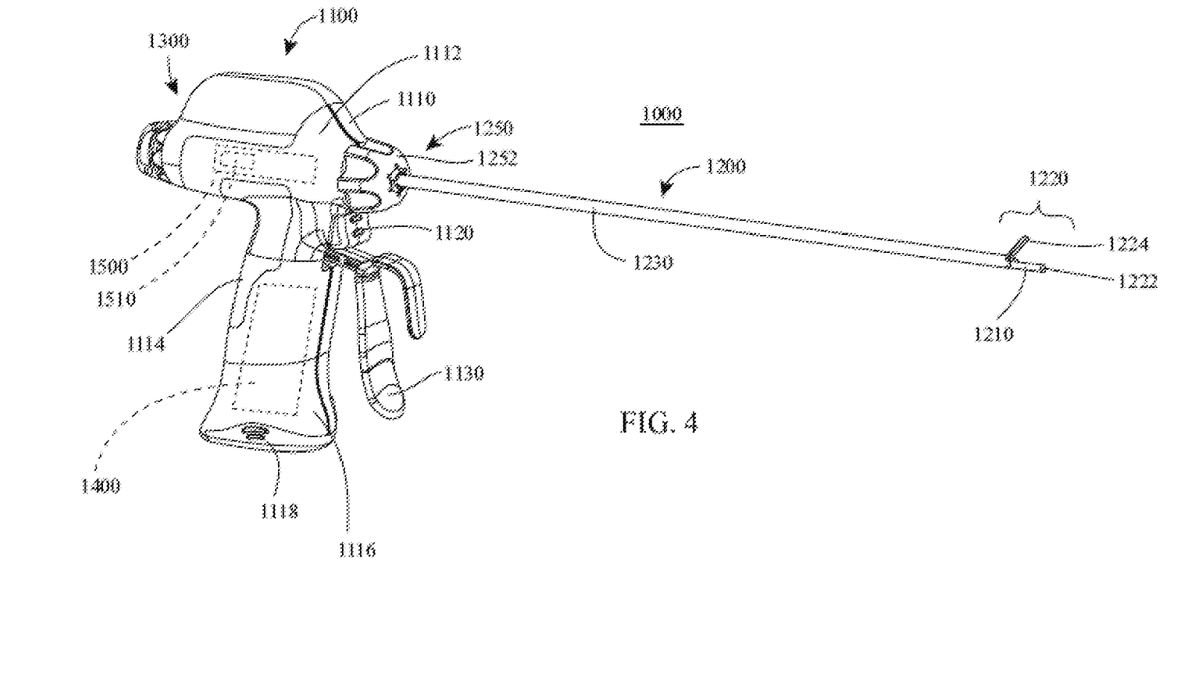
FIG. 4 is a side, perspective view of an ultrasonic surgical instrument including an onboard generator and battery in accordance with the present disclosure.

Referring to FIG. 4, ultrasonic surgical instrument 1000 generally includes a handle assembly 1100, an elongated assembly 1200 extending distally from handle assembly 1100, an ultrasonic transducer and generator assembly ("TAG") 1300 configured for releasable engagement with handle assembly 1100, a battery assembly 1400 configured for releasable receipt within handle assembly 1100, and a vacuum system 1500 operably disposed within or mounted on handle assembly 1100. Thus, ultrasonic surgical instrument 1000 is configured as a cordless, hand-held device. However, the present disclosure is equally applicable for use with corded ultrasonic surgical instruments configured to connect to a remote generator and/or vacuum source.

Handle assembly 1100 includes a housing 1110 defining a body portion 1112 configured to enable releasable mounting of TAG 1300 thereon and a fixed handle portion 1114 depending from body portion 1112. Fixed handle portion 1114 defines a battery compartment 1116 including a door 1118 configured to enable releasable receipt and enclosure of battery assembly 1400 within fixed handle portion 1114. Handle assembly 1100 further includes an activation button 1120 operably positioned to electrically couple between TAG 1300 and battery assembly 1400 when TAG 1300 is mounted on body portion 1112 of housing 1110 and battery assembly 1400 is enclosed within compartment 1116 of fixed handle portion 1114 of housing 1110 to enable selective energization of ultrasonic surgical instrument 1000, as detailed below.

A clamp trigger 1130 extends from housing 1110 of handle assembly 1100 adjacent fixed handle portion 1114 of housing 1110. Clamp trigger 1130 includes a drive portion (not shown) extending into body portion 1112 of housing 1110 and operably coupled to a drive assembly (not shown) to enable actuation of ultrasonic surgical instrument 1000 in response to actuation of clamp trigger 1130 relative to fixed handle portion 1114 of housing 1110, as detailed below.

Figure 5:
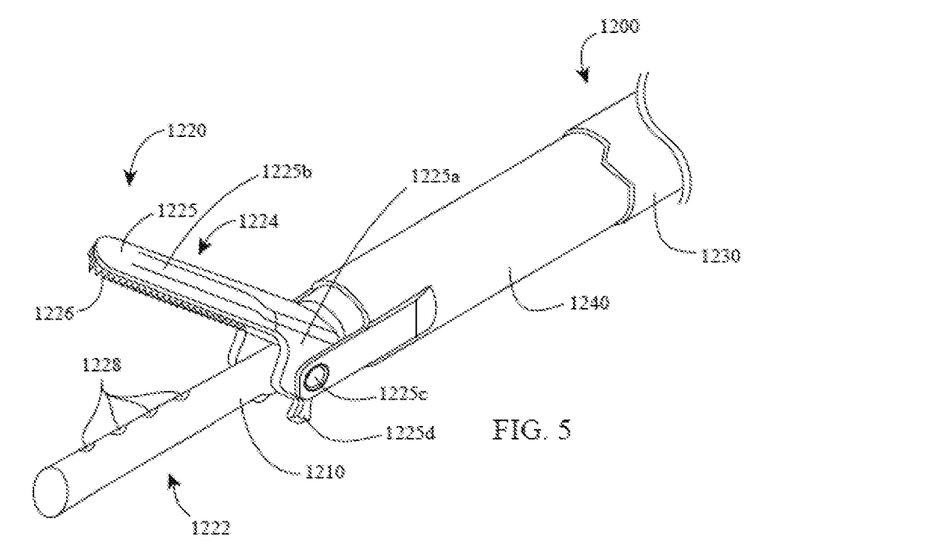
FIG. 5 is an enlarged, perspective view of a distal end portion of the ultrasonic surgical instrument of FIG. 4.
Figure 6:
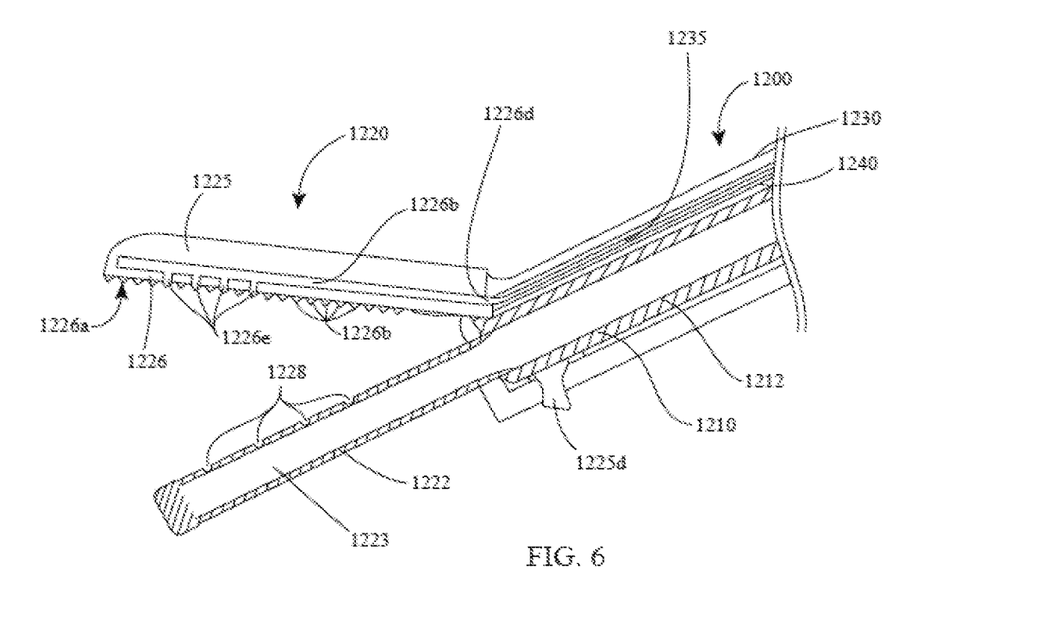
FIG. 6 is a perspective, longitudinal, cross-sectional view of the distal end portion of the ultrasonic surgical instrument of FIG. 4.

With additional reference to FIGS. 5 and 6, elongated assembly 1200 of ultrasonic surgical instrument 1000 includes a waveguide 1210 which extends from housing 1110 to an end effector 1220 disposed at the distal end portion of elongated assembly 1200. Elongated assembly 1200 further includes an outer shaft 1230 and an inner shaft 1240.

Waveguide 1210 includes a body portion 1212 that extends through housing 1110 and shafts 1230, 1240 and a distal end portion that extends distally from shafts 1230, 1240 and defines blade 1222 of end effector 1220. Waveguide 1210 further defines a lumen 1223 extending longitudinally therethrough, as detailed below. A proximal end portion of lumen 1223 is disposed in communication, e.g., via one or more tubes, seals, and/or other connectors (not shown), with vacuum system 1500. Thus, with lumen 1223 disposed in communication with vacuum system 1500, upon activation of vacuum system 1500, negative pressure is created within lumen 1223. Vacuum system 1500 may include a collection reservoir 1510, or a separate collection reservoir (not shown) may be provided, to collect any fluids and tissue debris aspirated from the surgical site through lumen 1223, as detailed below. The proximal end portion of body portion 1212 of waveguide 1210 includes features, e.g., threading, configured to enable operable engagement thereof with TAG 1300, e.g., with a female threaded receiver of the transducer of TAG 1300.

Outer shaft 1230 and inner shaft 1240 may cooperate to define a longitudinally-extending annular channel therebetween or may include a longitudinally-extending tube 1235 disposed in the annular space defined therebetween (as shown). A proximal end portion of tube 1235 is disposed in communication, e.g., directly or via one or more tubes, seals, and/or other connectors (not shown), with vacuum system 1500. Thus, with tube 1235 disposed in communication with vacuum system 1500, upon activation of vacuum system 1500, negative pressure is created within tube 1235.

Outer shaft 1230 is slidably disposed about inner shaft 1240 and waveguide 1210 and extends between housing 1110 and end effector 1220. Inner shaft 1240 is longitudinally fixed relative to housing 1110 and end effector 1220. A rotating assembly 1250 is rotatably mounted on housing 1110 and operably coupled to elongated assembly 1200 so as to enable rotation of elongated assembly 1200 and, thus, end effector 1220 relative to housing 1110 upon rotation of rotation wheel 1252 of rotating assembly 1250 relative to housing 1110.

End effector 1220, as noted above, is disposed at a distal end portion of elongated assembly 1200 and includes blade 1222 of waveguide 1210 and a jaw member 1224. Jaw member 1224 is pivotable supported at a distal end portion of inner shaft 1240 and is pivotable relative to blade 1222 between an open position, wherein jaw member 1224 is spaced-apart from blade 1222, and a closed position, wherein jaw member 1224 is approximated relative to blade 1222 in juxtaposed alignment therewith for clamping tissue therebetween.

Figure 7A:
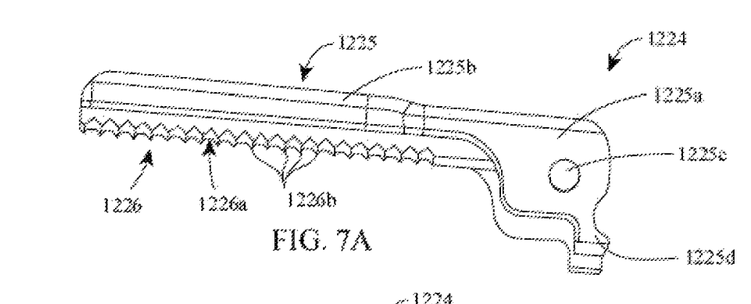
FIG. 7A is a side view of a jaw member of the ultrasonic surgical instrument of FIG. 4.
Figure 7B:
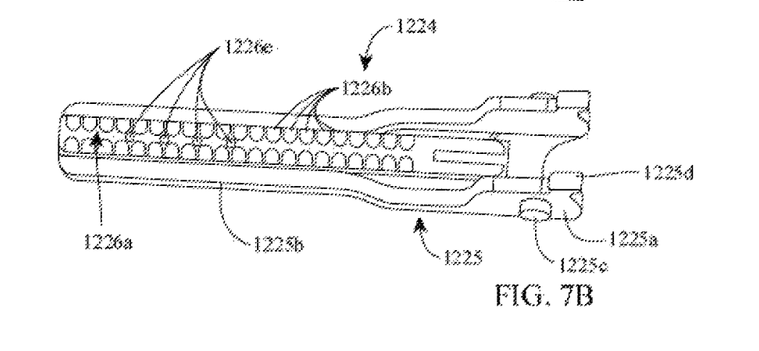
FIG. 7B is a bottom view of the jaw member of FIG. 7A.
Figure 7C:
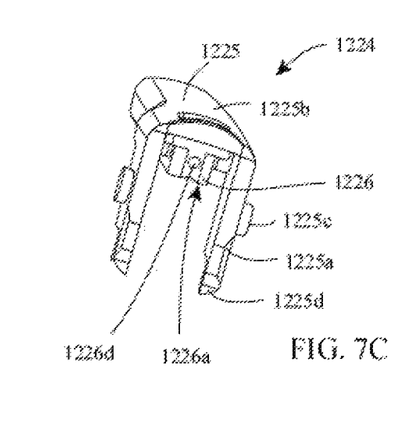
FIG. 7C is a proximal end view of the jaw member of FIG. 7A.

Referring to FIGS. 7A-7C, in conjunction with FIGS. 5-6, jaw member 1224 includes a structural body 1225 and a jaw liner 1226 secured to structural body 1225. Structural body 1225 may be formed from a rigid material and includes a proximal flange portion 1225a and an elongated distal portion 1225b extending distally from proximal flange portion 1225a. Proximal flange portion 1225a includes pivot bosses 1225c to enable pivotable coupling of jaw member 1224 with inner shaft 1240. Proximal flange portion 1225a further includes feet 1225d that enable operable coupling of jaw member 1224 with the distal end portion of outer shaft 1230 such that sliding of outer shaft 1230 about inner shaft 1240 pivots jaw member 1224 relative to blade 1222 between the open position and the closed position. Outer shaft 1230, in turn, is operably coupled to clamp trigger 1130 by way of the drive assembly (not shown) such that, in response to actuation of clamp trigger 1130 relative to fixed handle portion 1114 of housing 1110 of handle assembly 1100, jaw member 1224 is pivoted relative to blade 1222 between the open position and the closed position.

Elongated distal portion 1225b of structural body 1225 retains jaw liner 1226. Jaw liner 1226 may be formed from a compliant material and is positioned to oppose blade 1222 such that blade 1222 is inhibited from contacting structural body 1225 of jaw member 1224. As a result, the transfer of ultrasonic vibrations and/or thermal energy from blade 1222 to structural body 1225 during use is reduced.

Jaw liner 1226 defines a tissue-contacting surface 1226a and may include a plurality of gripping teeth 1226b disposed along the length of tissue-contacting surface 1226a. Jaw liner 1226 further defines a lumen 1226c extending longitudinally therethrough having a closed distal end. Lumen 1226c defines an open proximal end 1226d disposed in communication with tube 1235, e.g., directly or via one or more tubes, seals, and/or other connectors (not shown). A plurality of openings 1226e defined through tissue-contacting surface 1226a along the length thereof in spaced-apart relation relative to one another are disposed in communication with lumen 1226c. With openings 1226e disposed in communication with lumen 1226c which, in turn, is disposed in communication with tube 1235, upon activation of vacuum system 1500 (FIG. 4), negative pressure is created within tube 1235 and lumen 1226c so as to provide aspiration through openings 1226e, lumen 1226c, and tube 1235.

Figure 8:
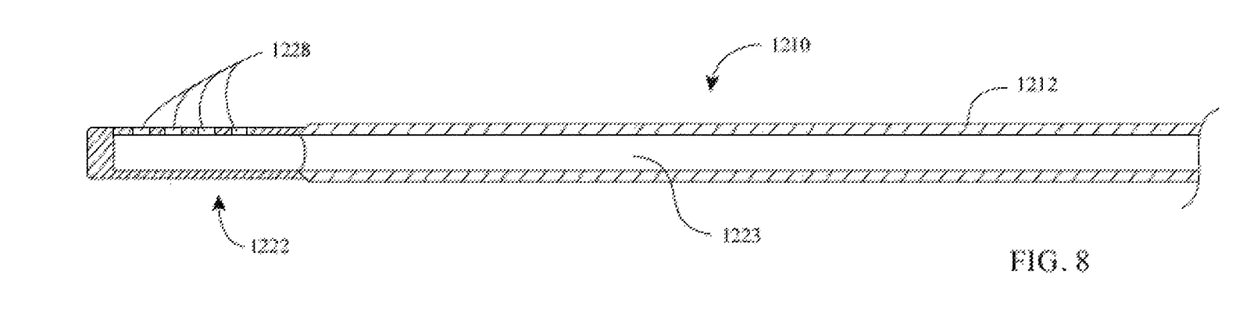
FIG. 8 is a longitudinal, cross-sectional view of a waveguide of the ultrasonic surgical instrument of FIG. 4.

Referring to FIG. 8, in conjunction with FIGS. 5-6, blade 1222 is configured to serve as an active or oscillating ultrasonic member that is selectively activatable to ultrasonically treat tissue grasped between blade 1222 and jaw liner 1226 of jaw member 1224. Blade 1222 may be formed to define a straight configuration or, alternatively, a curved configuration. Lumen 1223 of waveguide 1210 extends at least partially through blade 1222 and defines a closed distal end portion. A plurality of openings 1228 are defined through the tissue-contacting surface of blade 1222 oriented towards jaw member 1224. Openings 1228 are disposed along the length of blade 1222 in spaced-apart relation relative to one another and are disposed in communication with lumen 1223. With openings 1228 disposed in communication with lumen 1223, upon activation of vacuum system 1500 (FIG. 4), negative pressure is created within lumen 1223 so as to provide aspiration through openings 1228 and lumen 1223.

Referring again to FIG. 4, TAG 1300 is configured to convert electrical energy provided by battery assembly 1400 into mechanical energy that is transmitted along waveguide 1210 to blade 1222. More specifically, TAG 1300 is configured to convert the electrical energy provided by battery assembly 1400 into a high voltage alternating current (AC) waveform that drives the transducer (not shown) of TAG 1300. Activation button 1120 of handle assembly 1100, as noted above, is electrically coupled between battery assembly 1400 and TAG 1300. Activation button 1120 is selectively activatable in a first position and a second position to supply electrical energy from battery assembly 1400 to TAG 1300 for operating ultrasonic surgical instrument 1000 in a low-power mode of operation and a high-power mode of operation, respectively.

Referring generally to FIGS. 4-8, in use, with jaw member 1124 disposed in the open position relative to blade 1222, ultrasonic surgical instrument 1000 may be manipulated such that tissue to be treated, e.g., coagulated and/or dissected, is disposed between blade 1222 and jaw member 1224.

Once tissue to be grasped, treated, and/or divided is disposed between blade 1222 and jaw member 1224, clamp trigger 1130 may be actuated towards fixed handle portion 1114 of housing 1110 to pivot jaw member 1224 from the open position towards the closed position to grasp and/or manipulate tissue. With tissue grasped between blade 1222 and jaw member 1224 in the closed position of jaw member 1224, activation button 1120 may be activated to supply electrical energy from battery assembly 1400 to TAG 1300 such that TAG 1300 converts the electrical energy into ultrasonic energy that is transmitted along waveguide 1210 to blade 1222. The ultrasonic energy transmitted to blade 1222 ultrasonically vibrates blade 1222 to generate heat, thereby treating tissue grasped between blade 1222 and jaw member 1224. However, similarly as detailed above with respect to forceps 100 (FIG. 1), as a by-product of tissue treatment, high pressure and temperature steam may be produced and may escape, creating thermal spread.

In order to minimize or eliminate thermal spread, during the transmission of ultrasonic energy to blade 1222 (and, in embodiments, for a period after de-activation), vacuum system 1500 may be activated to apply vacuum through tube 1235 and lumen 1223 and, thus, at openings 1226e and 1228, respectively. As a result, the high pressure and temperature steam, as well as other heated fluids and/or tissue debris, are aspirated through openings 1226e and 1228, tube 1235 and lumen 1223, respectively, and into collection reservoir 1510, rather than spreading outwardly. Vacuum system 1500 may be activated automatically upon activation of activation button 1120, or manually.

Once tissue has been treated, jaw member 1224 may be returned to the open position to release the treated tissue.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

The invention claimed is:

1. A surgical instrument, comprising:
   an end effector assembly including a first grasping component defining a first tissue-contacting portion and a second grasping component defining a second tissue-contacting portion, at least one of the first or second grasping components movable relative to the other between an open position and a closed position, wherein, in the closed position, the first and second tissue-contacting portions cooperate to define a grasping area therebetween, at least one of the first or second tissue-contacting portions configured to apply energy to tissue disposed within the grasping area to treat tissue,
   wherein the first tissue-contacting portion defines a step including first and second surfaces offset relative to one another with a wall extending generally perpendicularly therebetween, the wall defining a first opening therethrough, the first opening disposed within the grasping area and in communication with a first lumen defined at least partially through the first grasping component, the first lumen adapted to connect to a source of vacuum to enable aspiration through the first opening.

2. The surgical instrument according to claim 1, wherein the second tissue-contacting portion defines a second opening therethrough, the second opening disposed within the grasping area and in communication with a second lumen defined at least partially through the second grasping component, the second lumen adapted to connect to a source of vacuum to enable aspiration through the second opening.

3. The surgical instrument according to claim 1, wherein the first tissue-contacting portion is configured to conduct radiofrequency (RF) energy through tissue disposed within the grasping area and to the second tissue-contacting portion.

4. The surgical instrument according to claim 1, further comprising:
   a housing; and
   at least one shaft extending distally from the housing, the at least one shaft supporting the end effector assembly at a distal end portion thereof,
   wherein the first lumen communicates with a shaft lumen extending through the at least one shaft, the shaft lumen adapted to connect to a source of vacuum to enable aspiration through the first opening.

5. The surgical instrument according to claim 1, further comprising:
   first and second shafts pivotably coupled to one another, the first and second shafts supporting the end effector assembly at distal end portions thereof,
   wherein the first lumen communicates with a first shaft lumen extending through the first shaft, the first shaft lumen adapted to connect to a source of vacuum to enable aspiration through the first opening.

6. A radiofrequency (RF) surgical instrument, comprising:
   an end effector assembly including a first jaw member defining a first tissue-contacting portion and a second jaw member defining a second tissue-contacting portion, at least one of the first or second jaw members movable relative to the other between an open position and a closed position, wherein, in the closed position, the first and second tissue-contacting portions cooperate to define a grasping area therebetween, the first and second jaw members adapted to connect to a source of RF energy to conduct RF energy between the first and second tissue-contacting portions and through tissue grasped within the grasping area to treat tissue,
   wherein the first tissue-contacting portion defines a step including first and second surfaces offset relative to one another with a wall extending generally perpendicularly therebetween, the wall defining a first opening therethrough, the first opening disposed within the grasping area and in communication with a first lumen defined at least partially through the first jaw member, the first lumen adapted to connect to a source of vacuum to enable aspiration through the first opening.

7. The RF surgical instrument according to claim 6, wherein the second tissue-contacting portion defines a second opening therethrough, the second opening disposed within the grasping area and in communication with a second lumen defined at least partially through the second jaw member, the second lumen adapted to connect to a source of vacuum to enable aspiration through the second opening.

8. The RF surgical instrument according to claim 6, further comprising:
   first and second shafts pivotably coupled to one another, the first and second shafts supporting the first and second jaw members, respectively, at respective distal end portions thereof,
   wherein the first lumen communicates with a first shaft lumen extending through the first shaft, the first shaft lumen adapted to connect to a source of vacuum to enable aspiration through the first opening.

9. The RF surgical instrument according to claim 8, wherein one of the first or second shafts supports a housing thereon at a proximal end portion thereof, the housing including an activation button, the activation button selectively activatable to supply RF energy to the first and second jaw members.

10. A surgical instrument, comprising:
    an end effector assembly defining first and second opposite lateral sides and including first and second jaw members extending longitudinally between the first and second lateral sides, the first jaw member defining a first tissue-contacting portion and the second jaw member defining a second tissue-contacting portion, at least one of the first or second jaw members movable relative to the other between an open position and a closed position, wherein, in the closed position, the first and second tissue-contacting portions cooperate to define a grasping area therebetween, the first and second tissue-contacting portions configured to cooperate to conduct radiofrequency energy through tissue grasped within the grasping area to treat tissue, wherein the first tissue-contacting portion defines a first opening therethrough, the first opening disposed within the grasping area and oriented towards the first lateral side of the end effector assembly.

11. The surgical instrument according to claim 10, wherein the second tissue-contacting portion defines a second opening therethrough, the second opening disposed within the grasping area and oriented towards the second, lateral side of the end effector assembly.

12. The surgical instrument according to claim 10, wherein the first jaw member defines a first lumen at least partially therethrough, and wherein the first opening is disposed in fluid communication with the first lumen.

13. The surgical instrument according to claim 10, wherein the first tissue-contacting portion includes a first surface and a second surface, and wherein the first opening is disposed between the first and second surfaces of the first tissue-contacting portion.

14. The surgical instrument according to claim 13, wherein a wall is defined between the first and second surfaces and extends generally perpendicularly therebetween, and wherein the first opening is defined through the wall.

15. The surgical instrument according to claim 13, wherein the first and second surfaces are offset relative to one another.

16. The surgical instrument according to claim 15, wherein the first and second surfaces and a wall disposed between the first and second surfaces define a step such that the first and second surfaces are offset relative to one another via the step.

17. The surgical instrument according to claim 10, further comprising at least one shaft supporting the end effector assembly at a distal end portion of the at least one shaft.

18. The surgical instrument according to claim 17, wherein one of the at least one shafts defines a shaft lumen extending therethrough, the shaft lumen disposed in fluid communication with the first opening.

* * * * *